(12) United States Patent
Luo et al.

(10) Patent No.: US 8,097,739 B2
(45) Date of Patent: Jan. 17, 2012

(54) PROCESS FOR THE MANUFACTURE OF NATURAL OIL HYDROXYLATES

(75) Inventors: Ning Luo, Fayetteville, AR (US); Trevor Newbold, Freeport (BS)

(73) Assignee: BioBases Technologies, LLC, Springdale, AR (US)

( * ) Notice: Subject to any disclaimer, the term of this patent is extended or adjusted under 35 U.S.C. 154(b) by 461 days.

(21) Appl. No.: 12/082,808

(22) Filed: Apr. 15, 2008

(65) Prior Publication Data
US 2008/0262259 A1    Oct. 23, 2008

Related U.S. Application Data (60) Provisional application No. 60/925,034, filed on Apr. 18, 2007.

(51) Int. Cl.
*C07C 231/00* (2006.01)
(52) U.S. Cl. ............................ 554/69; 564/123; 568/852
(58) Field of Classification Search .................... 554/69; 564/123; 568/852
See application file for complete search history.

(56) References Cited

U.S. PATENT DOCUMENTS

| | | |
|---|---|---|
| 2002/0058774 A1 | 5/2002 | Kurth et al. |
| 2003/0191274 A1 | 10/2003 | Kurth et al. |
| 2004/0209971 A1 | 10/2004 | Kurth et al. |
| 2006/0194974 A1 | 8/2006 | Narayan et al. |
| 2006/0276609 A1 * | 12/2006 | Lysenko et al. ............... 528/44 |
| 2007/0123725 A1 | 5/2007 | Lorenz |
| 2007/0173632 A1 | 7/2007 | Odaka |

FOREIGN PATENT DOCUMENTS

| | | |
|---|---|---|
| CN | 1837180 A | 9/2006 |
| CN | 1837181 A | 9/2006 |
| GB | 1248919 | 10/1971 |
| WO | WO2004/099227 | 11/2004 |
| WO | WO2005123798 | 12/2005 |
| WO | WO2006/094227 A2 | 9/2006 |

OTHER PUBLICATIONS

Fornol et. al. in Fornol, A.R.; Onah, E.; Ghosh, S.; Frazier, C.E.; Sohn, S.; Wilkes, G.L.; and Long, T.E., Synthesis and Characterization on Triglyceride-Based polyols and Tack-Free 15 Coatings Via The Air Oxidation of Soy Oil. J. Appl. Poly. Sci. (2006), 102:690-697.*

Guo, A.; Javni, I; Petrovic, Z., Rigid Polyurethane Foams Based on Soybean Oil. J. Appl. Poly. Sci. (2000), 77:467-473.*

Zlatanic, A.; Lava, C.; Zhang, W.; Petrovic, Z. S. Effect of Structure on Properties of Polyols and Polyurethanes Based on Different Vegetable Oils, 15 J. Poly. Sci.: Part B: Polymer Physics (2004), 42: 809-819.*

Guo, A.; Demydov, D.; Zhang, W.; Petrovic, Z. S. Polyols and Polyurethanes From Hydroformylation 5 of Soybean Oil, J. Polym. Environment (2002), i0 (112): 49-52.*

Tran, P.; Graiver, D.; Narayan, R. Ozone-Mediated Polyol Synthesis From Soybean Oil. Journal of the American Oil Chemists Society 5 (2005), 82 (9), 653-719.*

(Continued)

*Primary Examiner* — Deborah D Carr
(74) *Attorney, Agent, or Firm* — Stanley Baker (57) ABSTRACT

A process for preparing natural oil hydroxylates, the process comprising reacting an amino compound containing hydroxyl groups having a molecular weight of less than 200 Daltons with vegetable oil derived polyols.

23 Claims, 1 Drawing Sheet

OTHER PUBLICATIONS

Petrovic, Z. S.; Zhang, W.; Javni, I. Structure and Properties of Polyurethanes Prepared From Triglyceride Polyols by Ozonolysis, Biomacromolecules (2005), 6:713-719.*

Badri et al. In Production of a High-Functionality RBD Palm Kernel Oil-Based Polyester Polyol, Journal of Applied Polymer Science., Badri, K. H.; Ahmad, S.H.; Zakaria, S.(2001), 81(2), 384-389.*

Hu, Y.-H.; Gao, Y.; Wang, D.-N.; Hu, C.-P.; Zu, S.; Vanoverloop, L.; Randall, D. Rigid Polyurethane Foam 5 Prepared From a Rapeseed Oil Based Polyol, Journal of Applied Polymer Science (2002), 84(3), 591-597.*

U.S. Appl. No. 10/924,332, filed Aug. 23, 2004, Casper, et al.

* cited by examiner

FIG 2D ns as standards. The existence of molecular weight distribution is inherent in the natural oil origin. Polyols that are synthesized from this patent-pending process are typically natural oil polyols and they are commercially available, under the brand name Agrol®, from BioBased Technologies, LLC, Rogers, Ark.
PROCESS FOR THE MANUFACTURE OF NATURAL OIL HYDROXYLATES The present invention deals with a process for preparing natural oil hydroxylates, said process comprising reacting an amino compound containing hydroxyl groups having a molecular weight of less than 175 Daltons with vegetable oil derived polyols. This application claims priority from U.S. Provisional Patent Application Ser. No. 60/925,034, filed Apr. 18, 2007.

BACKGROUND OF THE INVENTION

Natural oil-derived polyols have been considered as alternatives for petroleum-based polyols for use in the polyurethane industry for making polyurethane materials. For making polyurethane materials, proton-activated groups, such as hydroxyl groups, are necessary for the reactions with isocyanate groups that result in urethane linkages. Almost all of the commodity vegetable oils, except for castor oil, unfortunately, contain no hydroxyl groups in their triacylglycerol structures of saturated and unsaturated fatty acids. However, the supply of castor oil is restricted because of its growth in limited geographical areas.

There is a need to chemically introduce hydroxyl groups onto the triacylglycerols of the vegetable oils for the uses in the polyurethane industry.

Polyurethanes are a class of polymeric materials with a wide spectrum of properties that make these materials of great use to the daily life of mankind. For example, polyurethanes are used in furniture, clothing, automotive, carpets, and many more applications in the form of foams, elastomers, coatings, adhesives, sealants, and composites.

In the U.S. patent application Ser. No. 10/924,332, filed on Aug. 23, 2004, Casper et al. claimed a simple, economic process to produce polyols from vegetable oils. The process is a "one-pot" process using acetic acid and hydrogen peroxide to oxidize the double bonds of the unsaturated fatty acids of the triacylglycerol structures thereby forming an epoxy group, and then conducting ring-opening of these epoxy groups in situ with acetic acid at an elevated temperature. The ring opening of an epoxy group with acetic acid generates a hydroxyl group and an adjacent acetate group simultaneously at the C9, C12, or C15 sites of C18-C22 fatty acid carbon chains. Because the hydroxyl groups are generated near the middle of the fatty acid chains, such hydroxyl groups are secondary hydroxyl groups.

No additional catalyst was needed in this process. No inorganic acids were used in this process as well. The final polyols produced from this process are composed of triacyl-glycerol structures as the basic units but somehow a portion of them can be linked together so that these dimer or higher oligomerized triacylglycerol units result in giving an average molecular weight of the polyols that is about twice as high as that compared with the unhydroxylated initial triacylglycerols.

In the triacylglycerol units of the polyols produced from this process, functional groups such as hydroxyl groups, acetate groups, and carbon-carbon double bonds exist in the final structural units. The physicochemical characteristics of the polyols produced from the above mentioned patent application are: hydroxyl numbers of 69-195 mg KOH/g, viscosity of 119-35000 cP at 25° C., Iodine numbers of 5-15 cgI$_2$/g, molecular weight of 1600-2200 Daltons, water solubility less than 0.004 percent weight/weight, freezing point 1-8° C., an acid number less than 1.0 mg KOH/g, a hydroxyl functionality from 2 to 7, no residual peroxides, and without inorganic acids. The molecular weight therein is a number-average molecular weight measured with GPC using narrow molecular weight distribution polystyrenes as standards. The existence of molecular weight distribution is inherent in the natural oil origin. Polyols that are synthesized from this patent-pending process are typically natural oil polyols and they are commercially available, under the brand name Agrol®, from BioBased Technologies, LLC, Rogers, Ark.

Monteavaro et al. in Monteavaro, L. L.; da Silva, E. O.; Costa, A. P. O.; Samios, D.; Gerbase, A. E.; Petzhold, C. "Polyurethane Networks from Formiated Soy Polyols: Synthesis and Mechanical Characterization. JAOCS (2005), 82: 365-371. (2005), prepared soy polyols with a one-step synthesis using formic acid and hydrogen peroxide on the double bonds of the vegetable oils (3/1.5/1).

This method followed the reaction steps of epoxidation of unsaturated fatty acids followed by ring-opening of the epoxy groups to form polyols. By simply varying the reaction time at 65° C., the polyols that were formed had hydroxyl numbers that ranged from 53-162, acid numbers of 1.2-2.2 and viscosities in the range of 230-9844 cP. Molecular weights of the polyols were reported up to 2404 Daltons. Based on the description in this publication, the structure of the resultant polyol is in the category of hydroxylated vegetable oil esters; however, the process forms a formic acid ester which is different than the acetic esters formed in the process of patent application Ser. No. 10/924,332 A1 mentioned Supra.

U.S. patent application 2007/0123725 A1 describes a process for the preparation of polyols based on natural oils converting unmodified unsaturated fatty acid triglycerides into polyols with peroxycarboxylic acids wherein phosphoric acid is used as a catalyst and followed by an additional alkoxylation step. In the step of preparing natural oil polyols and any further steps to modify the described natural oil polyols, no amines or hydroxyalkylamines were used in this patent application to form natural oil hydroxylates.

Fornol et. al. in Fornol, A. R.; Onah, E.; Ghosh, S.; Frazier, C. E.; Sohn, S.; Wilkes, G. L.; and Long, T. E., Synthesis and Characterization on Triglyceride-Based polyols and Tack-Free Coatings Via The Air Oxidation of Soy Oil. J. Appl. Poly. Sci. (2006), 102:690-697, applied dry-air oxidization on soybean oil to make polyols with hydroxyl numbers ranging from 7 to 110 mg KOH/g. Dry-air processes generated hydroxyl groups through the reactivity of adjacent protons of the double bonds on the unsaturated fatty acids. This can lead to natural oil polyols produced without additional ester formation.

U.S. Patent publication 2002/0058774 in the name of Thomas Kurth, et al describes a method to produce vegetable oil polyols in a transesterification process from a vegetable oil polyol with a multifunctional alcohol to form a polyol with selectable functionality.

WO Publication 2006/094227 A2 and U.S. Patent publication 2007/0173632 describes a method using an iron-containing catalyst in an oxidation process to produce natural oil-derived polyols having an increased hydroxyl number in which the hydroxyl number was as high as 220 mg KOH/g.

Guo and Petrovic et al. described in Guo, A.; Javni, I; Petrovic, Z., Rigid Polyurethane Foams Based on Soybean Oil. J. Appl. Poly. Sci. (2000), 77:467-473 the preparation of soy polyols via the oxirane/epoxide ring-opening reaction of epoxidized soybean oil with methanol. Methanol attacks the epoxy ring to generate a hydroxyl group and simultaneously form an adjacent ether bond on the fatty acid carbon chain. Therefore, such polyols are classified as hydroxylated vegetable oil ethers. The polyols had hydroxyl numbers ranging from 184-215 mg KOH/g and a viscosity ranging from 7200 to 10400 cP at ambient.

In another method, Zlatanic et al. in Zlatanic, A.; Lava, C.; Zhang, W.; Petrovic, Z. S. Effect of Structure on Properties of Polyols and Polyurethanes Based on Different Vegetable Oils, J. Poly. Sci.: Part B: Polymer Physics (2004), 42: 809-819, synthesized several polyols with epoxidation of the unsaturated fatty acid of oils followed by ring-opening of the epoxy groups in boiling methanol in the presence of tetrafluoroboric acid catalyst. The new oils were derived from canola, sunflower, soybean, linseed, sunflower, and corn oil. The hydroxyl numbers were determined to be 173.6 to 247.8 with a viscosity range of 1850-18200 cP at 27° C. In U.S. Pat. No. 6,107,433, Petrovic, et al. prepared vegetable oil-based polyols by adding a peroxyacid to a vegetable oil to give epoxidized vegetable oils and then this epoxidized vegetable oil was added to a mixture of an alcohol, water, and a catalytic amount of fluoroboric acid so as to form a vegetable oil-based polyol. The polyols prepared from this method had hydroxyl numbers ranging from 110-213 mg KOH/g and a viscosity ranging from 1000 to 7000 cP at room temperature. The above methods are multi-step processes. The polyols synthesized from the ring-opening with alcohols are hydroxylated vegetable oil ethers, which are different than hydroxylated vegetable oil esters in chemical composition.

Guo and Petrovic et al. in Guo, A.; Demydov, D.; Zhang, W.; Petrovic, Z. S. Polyols and Polyurethanes From Hydroformylation of Soybean Oil, J. Polym. Environment (2002), 10 (112): 49-52, utilized rhodium-catalyzed hydroformylation to synthesize two polyols with hydroxyl number of at 160 and 230 mg KOH/g. Hydroformylation generates a hydroxymethyl group adjacent to the carbon-carbon double bonds of the unsaturated fatty acids without generation of either additional ester or ether bonds, and thus the structure of the resultant polyol is different from either hydroxylated vegetable oil esters or hydroxylated vegetable oil ethers. Vegetable oil-derived polyols prepared from this hydroformylation method is also described in US 2006/0276609 A1. This is a multiple-step process because methyl ester formation, hydroxyformylation, and then use of the methyl ester to react with polyol, polyamine, or aminoalcohol are conducted as separated steps. In this process, amines were used to react with hydroxymethylated-fatty acid methyl esters (monomer). The reacting site for amine reactants is the methyl ester of the monomer in this patented process. One major disadvantage of this process is the generated methanol needs to be removed from the final product for polyurethane applications.

In U.S. patent application US 20060194974 A1, Narayan et. al. prepared polyols by the reaction of vegetable oil with ozone in a reaction mixture of alcohols and alkaline catalysts to cleave double bonds in fatty acid groups of the triglyceride. The polyols had 0.5-5.0 hydroxyl groups per triglyceride units as they claimed. However, no viscosity data was reported.

The synthesis of soybean oil-derived polyols from an ozone-mediated process has been disclosed by Tran et al in Tran, P.; Graiver, D.; Narayan, R. *Ozone-Mediated Polyol Synthesis From Soybean Oil. Journal of the American Oil Chemists' Society* (2005), 82(9), 653-719.

Petrovic et al. in Petrovic, Z. S.; Zhang, W.; Javni, I. Structure and Properties of Polyurethanes Prepared From Triglyceride Polyols by Ozonolysis, Biomacromolecules (2005), 6: 713-719, prepared soy polyols by ozonolysis from three oils. The hydroxyl numbers for trilinolein canola oil, soybean oil, and canola oil were 298, 228, and 260 mg KOH/g, respectively. The three polyols were solids at ambient temperature. Ozonolysis cleaves the unsaturated fatty acids to give shorter unsaturated fatty acids and therefore, vegetable oil-derived polyols prepared from ozonolysis compose triacylglycerols with lower molecular weights than the regular triacylglycerols in vegetable oils. In addition to the difference in the molecular weight, hydroxyl groups prepared from the ozonolysis are located at the ends of the fatty acid carbon chains thereby making them primary hydroxyls, whereas the hydroxyl groups prepared from the ring opening of epoxy groups, such as using the process described in the U.S. patent application Ser. No. 10/924,332, are located almost always at the C9 or C10, C12 or C13, and/or C15 or C16 carbon of the fatty acid carbon chains.

Kurth et al. claimed in the US patent applications U.S. 2003/0191274 and 2004/0209971 A1 that the functionality of blown soy oil was increased when glycerin was transesterified by the use of specific saccharides, for example, sucrose. The process described in these two patent applications is based on oxidation without using amines and/or hydroxyalkylamines.

Dwan'Isa et al. in WO 2004/099227 A2, Jena-pierre, L. Dwan'Isa, Lawrence T. Drzal, Amar K. Mohanty, Manjusri Misra, (Michigan State Univ. 2004), Polyol Fatty Acid Polyesters Process and Polyurethanes Therefrom, describe a solvent-free process for making a polyol fatty acid polyester compositions useful for the preparation of polyurethanes. These compositions were preferably made by reaction of natural oil with a multi-functional hydroxyl compound derived from a natural source, such as sorbitol, in the presence of an alkali metal salt or base such as potassium hydroxide. The latter compound serves as a catalyst which also acts to saponify the reaction mixture. The hydroxyl numbers of the polyols that could be obtained were as high as 434 mg KOH/g. The process described in this patent application is a transesterification process in nature. Similar processes can also be seen in the US patent application US 2002/0058774. In these patent documents viscosity values of the polyols were not given.

Wolff et al. in GB 1248919, (1968), describe Polyurethanes derived from fatty acid derivatives and also describe a method in GB 1248919A to prepare polyols from the reaction of a fatty acid or fatty acid methyl ester with diethanolamine, in which the hydroxyl numbers of the polyols are below 200 mg KOH/g. Viscosity values of these polyols were not reported. At least 80% of alcohols formed from the reaction were removed as described in one claim of the patented method.

Badri et al. in Production of a High-Functionality RBD Palm Kernel Oil-Based Polyester Polyol, Journal of Applied Polymer Science., Badri, K. H.; Ahmad, S. H.; Zakaria, S. (2001), 81(2), 384-389, synthesized refined, bleached, and de-odorized palm kernel oil-derived polyol by reaction of the oil with sorbitol and ethanolamine (70/30 ratio) with potassium octanoate as catalyst and ethylene glycol as emulsifier. The polyol was obtained with a viscosity of 1313 cP at 25° C. and the hydroxyl number ranged from 450-470 mg KOH/g. This process directly used the oil as the raw material, therefore, there are no hydroxyl groups initially present on the carbon chains of the fatty acids. A process, similar to Badri's method, but using soybean oil, is described in the Chinese patent application CN 1869184A. Again, there were initially no hydroxyl groups present on the carbon chains of the fatty acids.

Jenkines describes in WO 2005123798 a method of making carpet backings using fatty acid amide polyols. The inventor therein demonstrated that fatty acid amide polyols allow a significant replacement of conventional polyols with polyols derived from annually renewable resources, while maintaining important properties like edge curl, tuft bind, viscosity, and curing rates. The inventor mentioned GB 1248919 as supporting literature for the synthesis of the fatty acid amide polyols. In his description, the fatty acid esters used for preparing said fatty acid amide polyols can be obtained in a transesterification reaction between the oil or fat and a lower alcohol such as methanol or ethanol.

From his description, the resulting amide polyol typically contains a hydrocarbon tail corresponding to the initial fatty acid starting material (no hydroxyl group), and hydroxyl groups having a spatial relationship to each other that is defined by the structure of the starting alkanolamine compound. The hydroxyl equivalent weight is generally in the range of 125-225, preferably about 150-200. The fatty acid amide polyols used in the patent application WO 2005123798 are commercially available products from Ele & Pelron Corp., Lyons, Ill., having trade names PEL-AMID 676A (hydroxyl number 168 mg KOH/g), PEL-AMID 676 (hydroxyl number 110 mg KOH/g), and PEL-SOY744 (hydroxyl number 440 mg KOH/g). PEL-AMID 676A and 676 are ethoxylated products. PEL-SOY744 has a high hydroxyl number of 440 because it is blended with approximately 10% of glycerine.

Chinese patent application CN 1837180A describes a method of making biobased polyol from rapeseed oil. The first step of this method is an alcoholysis reaction with multiple alcohol and rapeseed oil with alkali hydroxides as catalysts to form mono-fatty acid esters. Epoxidation is then conducted on the alcoholyzed unsaturated fatty acids with organic peroxides. The third step is the ring-opening of the epoxy groups with proton-activated compounds including amines and ethanolamines. Water washing and purification steps are also used between or after each reaction step and prior to each reaction step to get a final polyol product. This is obviously a multiple step process. Amines and ethanolamines are used herein in the third step to open the epoxy rings formed on the unsaturated fatty acid mono-esters. The most preferred ethanolamines are those with tertiary amines such as triisopropanolamine, triethanol-amine, methyl diethanolamine, and methyl diisopropanolamine as disclosed.

CN 1837181A describes a method of making biobased polyol from rapeseed oil, in which the method promotes the epoxidation of rapeseed oil with organic peroxides, ring-opening of epoxy groups with alcohols, and then alcoholysis with multiple alcohols including ethanolamines. The use of water washing and purification steps are utilized after each reaction step and prior to each reaction step to obtain the final polyol product. The most preferred ethanolamines are those with tertiary amines such as triisopropanolamine, triethanolamine, methyl diethanolamine, and methyl diisopropanolamine as disclosed. In this complicated process, hydroxyl numbers of the final polyols can be higher than 500 mg KOH/g.

Hu et al. in Hu, Y.-H.; Gao, Y.; Wang, D.-N.; Hu, C.-P.; Zu, S.; Vanoverloop, L.; Randall, D. Rigid Polyurethane Foam Prepared From a Rapeseed Oil Based Polyol, Journal of Applied Polymer Science (2002), 84(3), 591-597, reported a two-step method to synthesize polyols from rapeseed oil. In the first step, rapeseed oil was reacted with hydrogen peroxide and formic acid at 40° C.-50° C. for 1 hr and then was allowed to stand overnight for the separation of water and oil phases. The hydroxylated rape seed oil was formed with a hydroxyl number 100 mg KOH/g, acid number 5 mg KOH/g, and viscosity of 400 cP at 25° C. Then the hydroxylated rapeseed oil was reacted with triethanolamine using Lithium hydroxide as catalyst at 150° C. The authors declared this was an alcoholysis process of the hydroxylated rapeseed oil with triethanolamine to produce a polyol of hydroxyl number 367 mg KOH/g, acid number 0.14 mg KOH/g, and viscosity 1600 cP. The reaction of hydroxylated rapeseed oil with ethanolamine and diethanolamine is also demonstrated as a side reaction, which is due to the ethanolamine and diethanolamine existing in triethanolamine as impurities.

In brief, the polyols described in the above published literature normally have hydroxyl numbers lower than 250 mg KOH/g and a few have hydroxyl numbers higher than 200 mg KOH/g. The hydroxyl number is one of the key parameters that impacts the property of polyurethane materials made with such polyols. Viscosity is another parameter that can also have greater impact on the processing and production effectiveness and the mixing quality in the preparation of polyurethane materials. For example, it would be favorable to use polyols in a spray process or a reaction injection molding (RIM) process or high pressure molded foam process. Therefore, there is a need to synthesize polyols having a high hydroxyl number and at the same time offering relatively low viscosity in the range of 100-10,000 cP at 25° C. In the preparation of vegetable oil-derived polyols via epoxidation reaction of double bonds, the hydroxyl number relates to the consumption of double bonds in the unsaturated fatty acid chains and it is normally difficult to obtain a vegetable-oil-derived polyol with a hydroxyl number higher than 250 mg KOH/g. On the other hand, one generally finds that higher hydroxyl containing polyols also give a higher viscosity. It is a challenge to synthesize vegetable oil-derived polyols with high hydroxyl number and low viscosity.

THE INVENTION

One embodiment of the invention disclosed herein is a process for preparing natural oil hydroxylates. The process comprises reacting an amino compound containing hydroxyl groups having a molecular weight of less than 200 Daltons, with natural vegetable oil polyols at a time sufficient and a temperature sufficient, under vacuum, to provide natural oil hydroxylates having hydroxyl number values ranging from 240 to 530 mg KOH/g and a viscosity ranging from 260-5300 cP at 25° C.

In a second embodiment, the invention comprises the above-described process and including a catalyst.

In another embodiment, there is a process for preparing natural oil hydroxylates. The process comprises reacting an amino compound containing hydroxyl groups having a molecular weight of less than 200 Daltons with vegetable oil derived polyols wherein the vegetable oil derived polyols are derived by a process comprising contacting a raw vegetable oil with hydrogen peroxide and an organic acid in the presence of water for a sufficient period of time, a sufficient temperature, and a sufficient pressure to form hydroxyl groups from unsaturated moieties in the vegetable oil, and thereafter separating any volatiles from the hydroxylated functional vegetable oil, wherein the organic acid has from 1 to 3 carbon atoms.

In a further embodiment, there is a process for preparing natural oil hydroxylates as described just above, using a catalyst.

Still another embodiment is a process that uses natural vegetable oil that contains 0-94 weight percent of hydroxylated fatty acid hydroxyalkylamide, 0-34 weight percent of hydroxylated mono-glyceride esters, 0-64 weight percent of hydroxylated diglyceride esters, and 0-16 weight percent of glycerol.

A further embodiment is a process wherein the natural vegetable oil contains 36-94 weight percent of hydroxylated fatty acid hydroxyalkylamide, 0-34 weight percent of hydroxylated mono-glyceride esters, 0-64 weight percent of hydroxylated diglyceride esters, and 0-6 weight percent of glycerol.

Yet another embodiment is a process wherein the natural vegetable oil contains 51-84 weight percent of hydroxylated fatty acid hydroxyalkylamide, 13-31 weight percent of hydroxylated mono-glyceride esters, 0-21 weight percent of hydroxylated diglyceride esters, and 0-3 weight percent of glycerol.

One other embodiment is a composition of matter that is a natural oil hydroxylate having a hydroxyl number value ranging from 240 to 530 mg KOH/g and a viscosity ranging from 260-5300 cP at 25° c.

Going to another embodiment, the invention comprises the use of the inventive natural oil hydroxylate of this invention to prepare polyurethane articles.

A final embodiment is the use of the inventive natural oil hydroxylates as surfactants and surfactant components.

DETAILED DESCRIPTION OF THE INVENTION

The present invention is a method for utilizing natural oil polyols as starting materials to react with hydroxyalkylamines for the production of polyols with increased hydroxyl numbers and intermediate viscosities. More specifically, the method of the invention is aminolysis by hydroxyalkylamines of the ester bond in natural oil polyols.

After the aminolysis process at elevated temperature, preferably in the presence of an organometallic catalyst, natural oil polyols were converted to natural oil hydrolyzates with increased hydroxyl numbers in the range of 240-530 mg KOH/g, and a viscosity in the range of 260-5530 cP at 25° C. (intermediate viscosities). Such hydroxylates are amber-colored liquids with improved reactivity and improved miscibility with natural oil polyols with lower OH numbers than conventional polyether polyols. When the inventive polyol is used in the preparation of polyurethanes, these polyurethane materials showed improved hardness.

"Natural oil hydroxylates" for the purpose of this invention, means those materials that are derived from natural vegetable oils and amino compounds having one or more hydroxyl groups attached thereto. The term "polyol" when modified by the adjective "inventive" is synonymous with the term "natural oil hydroxylate". Those skilled in the art will know from the context when the specification is referring to conventional polyols and those modified polyols (e.g., natural oil hydroxylates) of claimed invention.

Figure 1:
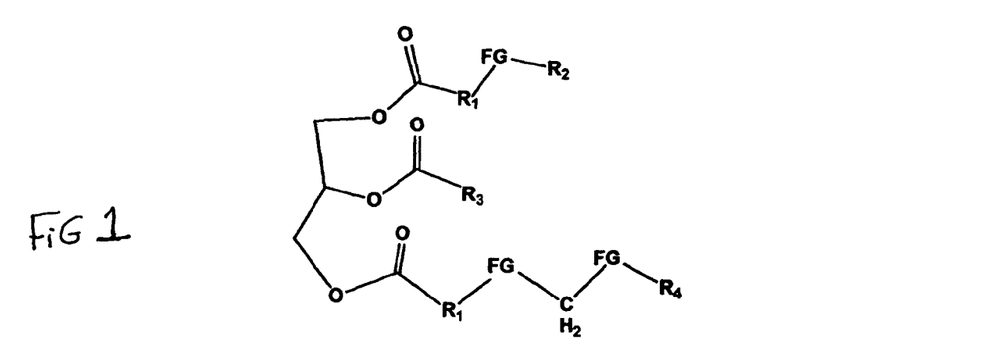
FIG. 1 is a general structure of the starting natural oil polyols showing a polyol having hydroxylated fatty acid triglyceride units.

FIG. 1 is a general structure of the starting polyols for the inventive process, wherein in FIG. 1, FG is selected from —CH(OH)—CH(OCOCH$_3$)—, —CH(OCOCH$_3$)—CH (OH)—, —(CH(OH)—CH(OH)—, and —CH$_2$=CH$_2$—; R$_1$ is —(CH$_2$)$_7$; R$_2$ is —(CH$_2$)$_7$—CH$_3$; R$_3$ is —(CH$_2$)$_{14}$—CH$_3$, and C$_{14}$-C$_{22}$ fatty acids, —R$_1$—FG—R$_2$, and —R$_1$—FG—CH$_2$—FG—R$_4$—; R$_4$ is —(CH$_2$)$_4$—CH$_3$; R$_5$ is —(CH$_2$)$_2$—, —CH$_2$CH(CH$_3$)—, and —CH$_2$CH(OH)CH$_2$—; R$_6$ is —(CH$_2$)$_2$OH, —CH$_2$CH(CH$_3$)OH—, —CH$_3$, —CH$_2$CH$_3$, —CH$_2$—C$_6$H$_5$, —C$_6$H$_5$—, —CH$_2$CH$_2$CH$_2$OH, —(CH$_2$)$_3$CH$_3$, or —C$_2$H$_4$—C$_6$H$_4$—, and H.

FIG. 2 shows generalized chemical structures wherein R$_7$ is R$_3$ or —COCH$_3$; R$_8$ is =CHCH$_2$OH or —CH$_2$CH(OH)—

The process provides for placing a predetermined amount of hydroxyalkylamines into a reactor containing natural oil polyols to conduct a reaction at 90-200° C., and if desired, including 0.05-0.2 weight percent of organometallic catalyst based on the weight of starting natural oil hydroxylates.

During the process of the polyol synthesis, no by-produced alcohols that are generated need to be removed from the reactor. No waste stream is generated from the process of the invention. After the reaction is completed, no further purification steps need to be used. Hydroxyl numbers of the resultant polyols are increased compared with that of the starting natural oil polyols.

Some of the natural oil polyols used in the invention are the products or the intermediates prepared from the process described in U.S. patent application Ser. No. 10/924,332, filed on Aug. 23, 2004 and the disclosure therein is hereby incorporated herein by reference for what it teaches about the compositions and their preparation. Such natural oil polyols have properties such as color of less than 12 Gardener reading, essentially no residual peroxides, less than 0.1% w/w water, an acid number of less than 10 mg KOH/g, essentially no inorganic acids, hydroxyl numbers of 69-195 mg KOH/g, viscosity of 119-35000 cP at 25° C., Iodine number of 5-115 cgI$_2$/g, molecular weight of 1600-2200 Daltons, water solubility less than 0.004% w/w, freezing point 1-8° C., and a functionality from 2 to 7. To analytically obtain these properties, the polyols were analyzed by using the AOCS Official Process of analysis, that is, AOCS Official Process, DC-3d-63 for acid number; AOCS Official Process, Cd 1-25 for determination of Iodine number of fats and oils, and AOCS Official Process, Cd 13-60 for hydroxyl number. Water content was determined by the AOCS official method Tb 2-64, and AOCS Official Process, Td 1a-64 for color Gardner 1963 (Glass Standard) was used. Natural oil hydroxylates with the above mentioned properties, but with an acid number equal to or less than 1 mg KOH/g, are commercially available from BioBased Technologies, LLC, under the brand name Agrol®. Natural oil hydroxylates with the above mentioned properties but the acid number higher than 1 mg KOH/g are also the intermediate products prepared from the process described in the U.S. patent application Ser. No. 10/924,332, filed on Aug. 23, 2004, and are provided by BioBased Technologies, LLC.

The molecular weights specified in this invention are defined as conventional number-average molecular weights. The molecular weight of a given polyol was measured using a Waters gel permeation chromatograph equipped with Waters 2487 dual λ absorbance detector, a Waters 2414 refractive index detector, and two Waters Styragel® HR 1 THF columns. The flow rate of the tetrahydrofuran eluent was 1 mL/min. at 40° C. Polystyrene standards (purchased from Waters) with narrow molecular weight distributions were used for molecular weight calibration and, therefore, the molecular weight results are relative molecular weights. The polystyrene standards were of molecular weight of 0.93×10$^3$, 1.05×10$^3$, 1.26×10$^3$, 1.31×10$^3$, 1.99×10$^3$, 2.97×10$^3$, 3.37× 10$^3$, 4.49×10$^3$, 4.92×10$^3$, and 5.03×10$^3$ Daltons.

Because of the use of intermediate products, the method of the invention can be easily integrated into the process described in the U.S. patent application Ser. No. 10/924,332 to form polyols with similar specifications. In the process that is described in the U.S. patent application Ser. No. 10/924, 332, filed on Aug. 23, 2004, vegetable oils containing saturated and unsaturated fatty acids were reacted with predetermined amounts of hydrogen peroxide and acetic acid at 90-130° C. Thereafter, aminolysis is conducted at an elevated temperature, and if desired, in the presence of an organometallic catalyst after all epoxy groups are completely consumed, and water and any excess amounts of acetic acid are completely removed.

Natural oils that can be used for conversion into natural oil hydroxylates are those that contain triacylglycerols of saturated and unsaturated fatty acids. Examples include but are not limited to soybean oil, castor oil, palm oil, rapeseed oil, cotton oil, corn oil, sunflower oil, olive oil, canola oil, peanut oil, coconut oil, algae oil, and jatropha oil. Preferable vegetable oils are soybean oil, canola oil, jatropha oil, algae oil, and palm oil.

Hydroxyalkylamines useful in the present invention are those having primary, secondary, tertiary, and cyclic amine groups combined with at least one hydroxyl group in their molecular structures and having molecular weights ranging from 74 to 166 Daltons. Preferred hydroxyalkylamines are hydroxyalkylamines with at least one hydroxyl group as well as one secondary amine group in a single molecule.

For the purpose of the invention, such hydroxylkyamines include but are not limit to methylaminoethanol, diethanolamine, 2-(ethylamino)ethanol, N-benzylethanolamine, 2-anilimoethanol, 3-pyrrolidinol, prolinol, 3-piperidinol, 2-(isopropylamino)-ethanol, 1-(2-hydroxyethylamino)propanol, 3-methylamino-1,2-propanediol, 2-piperidinemethanol, 2-(tert-butylamino)ethanol, 2-(butylamino)ethanol, 1-(2-aminoethylamino)-2-propanol, 2-(3-aminopropylamino)ethanol, 3-(−2-hydroxyethylamino)-1-propanol, and 2-(2-ethylanilimo) ethanol, diisopropanolamine, 2-(2-(Methylamino)-ethylamino)ethanol, pyrrolidinol, prolinol, piperidinol, piperidinemethanol, and any combinations of these hydroxyalkylamines.

The organometallic catalysts useful in the present invention are titanates. Examples of such titanates include but are not limit to titanium ethoxide, titanium isopropoxide, titanium n-propoxide, titanium n-butoxide, titanium 2-ethylhexoxide, titanium isobutoxide, and titanium butoxy isopropoxy, or other titanates. Such titanates are commercially available under the trade name of Tyzor® (DuPont™, Tyzor@usa.dupont.com) or Vertec®, Johnson Matthey Catalysts, 4106 New West Rd, Pasadena, Tex. 77507-1882.

The amount of the catalysts is in the range of 0.05-0.20 weight percent based on the weight of the starting hydroxylated vegetable oil esters. Preferred is the use of the catalyst at 0.1% weight percent.

The reaction is carried out at a temperature of from 90-200° C. and the preferred range is a temperature of about 140-150° C.

While the aminolysis reaction can be performed without using a titanate catalyst, it was found surprisingly, that the resultant polyols made with titanate catalysts showed better freeze/thaw stability.

The resultant polyols were amber-colored liquids with the hydroxyl number hydroxyl number from 240-530 mg KOH/g and viscosity values from 260 to 5530 cP at 25° C. The starting polyol, hydroxyalkylamines, and the combination of hydroxyalkylamines need to be carefully selected. It is also disclosed in this invention that with a selected hydroxy-alkylamines as aminolysis agent, the viscosity of the resultant polyol can be as low as 260 cP at 25° C.

Figure 2A:
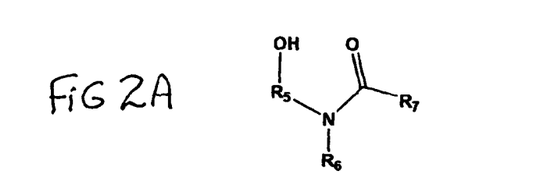
FIG. 2A is a generalized chemical structure showing hydroxylated fatty acid hydroxyalkylamide structures.
Figure 2B:
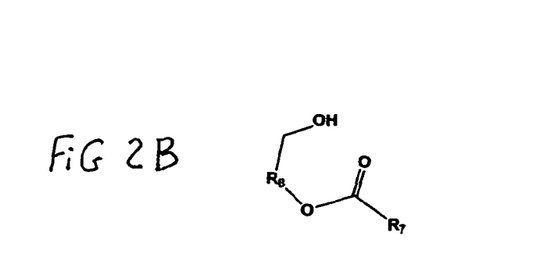
FIG. 2B is a generalized chemical structure showing hydroxylated mono-glyceride esters.
Figure 2C:
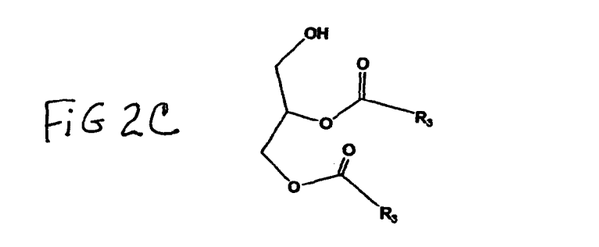
FIG. 2C is a general chemical structure of hydroxylated diglyceride esters.
Figure 2D:
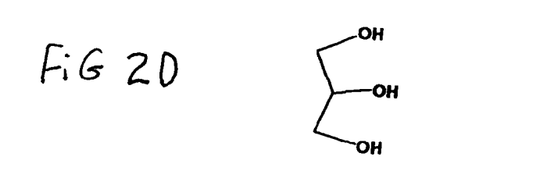
FIG. 2D shows the chemical structure for glycerol.

There are two kinds of ester bonds, glycidic ester and acetic ester that are part of the molecular structure of the starting polyols. After the reaction of a hydroxyalkylamine with the glycidic ester bonds, the triacylglycerol structures are broken down and converted to hydroxylated fatty acid hydroxyalkylamide structures (FIG. 2A), hydroxylated mono-glyceride esters (FIG. 2B), hydroxylated diglyceride esters (FIG. 2C), and glycerol (FIG. 2D). When hydroxyalkylamines attack the acetic acid ester bonds, a hydroxyalkyl acetamide will be formed. Meanwhile, a secondary hydroxyl group will be generated at the original acetate site. Such a reaction is also suitable for modification of other types of natural oil hydroxylates, for example, hydroxylated vegetable oil ethers, as starting polyols. However, because no acetate group exits in such natural oil hydroxylates, there will be no formation of hydroxyalkyl acetamides when such other natural oil hydroxylates are used as starting materials.

As discussed earlier, hydroxyl groups exist in the fatty acid chains of the natural oil hydroxylates. These hydroxyl groups in the natural oil hydroxylates are secondary hydroxyl groups located near the middle of the fatty acid carbon chains. During the aminolysis promoted by hydroxyalkylamines with natural oil hydroxylates, such hydroxyl groups will remain unreacted. In addition to this, once acetamides are formed, additional hydroxyl groups will be generated adjacent to the original hydroxyl group. Therefore, the hydroxyl number values and the structure of the hydroxyl groups in the resultant polyols of the invention are defined not only by the structures of the hydroxyalkylamines, but also by the starting polyols, and the ratio of the hydroxyalkylamines with that of the starting polyols.

The resultant polyols are mixtures of the four major types of chemical components shown in FIG. 2. Polyols of the invention contain 0-94 weight percent of hydroxylated fatty acid hydroxyalkylamide (FIG. 2A), 0-34 weight percent of hydroxylated mono-glyceride esters (FIG. 2B), 0-64 weight percent of hydroxylated diglyceride esters (FIG. 2C), and 0-16 weight percent of glycerol (FIG. 2D). Preferred compositions of the resultant polyols contain 36-94 weight percent of hydroxylated fatty acid hydroxyalkylamide, 0-34 weight percent of hydroxylated mono-glyceride esters, 0-64 weight percent of hydroxylated diglyceride esters, and 0-6 weight percent of glycerol. The most preferred composition of the resultant polyols contain 51-84 weight percent of hydroxylated fatty acid hydroxyalkylamide, 13-31 weight percent of hydroxylated mono-glyceride esters, 0-21 weight percent of hydroxylated diglyceride esters, and 0-3 weight percent of glycerol. The polyols of the invention have hydroxyl numbers ranging from 240 to 530 mg KOH/g. The most preferred hydroxyl numbers range from 240 to 450 mg KOH/g while the most preferred viscosity range is from 260 to 6000 cP at 25° C. In order to produce the said polyols with the declared characteristics, the amount of hydroxyalkylamines that can be used in the aminolysis reaction step is 0.1-70 weight percent based on the weight of the starting hydroxylated vegetable oil esters. The preferred range is 6-70 weight percent based on the weight of hydroxylated vegetable oil esters, and the most preferred range is 9-36 weight percent based on the weight of the starting polyol.

This composition can also be described as the product consisting of a) fatty acid monoalkanolamide or fatty acid dialkanolamide; and b) natural oil diglyceride or natural oil monoglyceride or their mixtures, where fatty acid groups may also contain acetate, methoxide etc. groups. Additionally, the product compositions may contain up to total of 20% glycerin, the triglycerides and short chain ($C_1$-$C_5$) di- or monoalkanol-amides.

It is contemplated within the scope of this invention to carry out the processes of this invention using an inert blanket of gas during the reaction, said inert gas, for example, being nitrogen.

It is noted that vacuum is used in the processes of this invention, and for the purposes of this invention, the vacuum can range from 25 to 200 Torr for 0.5 to 3 hours.

The freeze/thaw stability testing of a polyol was similar to the protocol described in patent application US 2006/0041156 A1. That is, 80 grams of a neat polyol were placed into a 120 milliliter wide-mouth, clear, glass jar. The lid was securely tightened and the glass jar was placed into a −4° C. freezer for 4 hours. After the four hour period, the sample was removed from the freezer and allowed to warm up at ambient temperature (about 24° C.) until it returned to liquid status. Then the sample was visually observed for the presence of phase separation, precipitated particles, floating particles or a visible haze of any kind. The process was then repeated for at least 3 freeze/thaw cycles.

The inventive polyols can react with isocyanates to form polyurethanes with or without using catalysts. The isocyanates that can be used for the purpose of making polyurethane materials can be any molecule with more than one functional isocyanate group. Examples include, but are not limited to, any of the commercially available isocyanates such as toluene diisocyanate, methylene diphenyl diisocyanate, hexamethylene diisocyanate, and isophorone diisocyanate. Some of the most important properties of polyols are characterized in terms of reactivity, miscibility, and water miscibility. Hardness of the polyurethane material made from the inventive polyol is also compared with the starting natural oil hydroxylates. The inventive polyols posses increased reactivity and can be used to improve miscibility of the starting polyol with selected petroleum-based polyether polyols.

When solid polyurethane materials are made, the resultant polyurethane materials made with the inventive polyols show increased hardness compared with the materials prepared with the starting polyols.

The reactivity of the resultant polyols is characterized using gelation time using a Brookfield Viscosity Test (BVT) method. This BVT method measures viscosity increase with the reaction of polyols with liquefied MDI. To determine the reactivity characteristics of a polyol, a convenient size sample of the polyol (typically 100 grams) is placed into a 250 ml, wide mouth plastic cup. To this cup a 0.05 weight percent catalyst is added based on the polyol weight and then mixed using mechanical stirring for 30 seconds at 1000 RPM. After mixing the catalyst with polyol, a calculated amount of liquefied MDI (1.05 NCO index) is mixed for thirty (30) seconds on the same mixing equipment. After the end of the thirty (30) seconds mix, the cup is removed from the agitator, placed on the viscometer and the viscosity growth recorded over a 40-minute period. The collected time and viscosity data are plotted with a computer spreadsheet or graphics program to give a BVT Reactivity Curve for the polyol being tested. Gelation time is recorded at the time when viscosity reached 25000 cP on the viscosity-curing time plot. Gelation time is a measurement of reactivity of polyol with isocyanate. The less gelation time, the higher the reactivity of the polyol is.

A miscibility test is conducted by mixing two different polyols together in a single metric scale cylinder. The cylinder is then placed in a 70° C. oven for at least 12 hours and then removed from the oven and brought to room temperature for an additional 48 hours. Volumes of each phase are recorded. The miscibility refers to the solubility of the natural oil-derived polyols in conventional polyether polyols, which is calculated based on the volume ratio of the natural oil hydroxylates dissolved in 50 ml of the conventional polyether polyol.

Miscibility of natural oil hydroxylates with conventional polyols is a very important characteristic for the use of the natural oil hydroxylates in polyurethane applications because the composition of different polyols is used as a parameter to adjust physical properties in many polyurethane systems. When intimate mixing of two non-miscible liquids was observed with the help of the third liquid component (i.e. the inventive polyol), it generally implies that the third liquid component maximized surface interactions and brought intimate intermolecular interactions to the liquid-liquid system. In other words, the third liquid component must show surface activity between the two non-miscible liquids when an improvement on the miscibility is observed. The same test is also used for the characterization of the miscibility of water with the inventive polyols. Miscibility of water with polyols is a critical parameter for the development of water-blown polyurethane foams.

Polyurethane material is prepared by mixing the inventive polyol with isocyanates (at 1.05 NCO/OH molar ratio) with a mechanical agitator. The mixture is then transferred to a mold for curing at either ambient temperature or elevated temperature. The final solid polyurethane materials were aged 2 weeks at ambient atmosphere prior to any tests. Shore A and Shore D hardness were measured in compliance with the ASTM D2240-05 Standard Test Method for Rubber Property-Durometer Hardness.

EXAMPLES

The following materials were employed in the examples that follow:

Polyol-1: hydroxyl number 114 mg KOH/g, viscosity 530 cP at 25° C., Iodine number 92 $cgI_2/g$, acid number less than 1.0 mg KOH/g, water content less than 0.1% w/w, freezing point 2° C., water solubility less than 0.004% w/w, and molecular weight 1750 Daltons. This polyol is available from BioBased Technologies, LLC as Agrol® 3.6.

Polyol-2: hydroxyl number 124 mg KOH/g, viscosity 780 cP at 25° C., acid number less than 1.0 mg KOH/g, Iodine number 86 $cgI_2/g$, water content less than 0.1% w/w, freezing point 2° C., water solubility less than 0.004% w/w, and molecular weight 1830 Daltons. This polyol is available from BioBased Technologies, LLC as Agrol® 4.0.

Polyol-3: hydroxyl number 131 mg KOH/g, acid number less than 1.0 mg KOH/g, viscosity 1100 cP at 25° C., Iodine number 79 $cgI_2/g$, water content less than 0.1% w/w, freezing point 2° C., water solubility less than 0.004% w/w, and molecular weight 1848 Daltons. This polyol is available from BioBased Technologies, LLC as Agrol® 4.3.

Polyol-4: hydroxyl number 103 mg KOH/g, viscosity 320 cP at 25° C., acid number less than 1.0 mg KOH/g, Iodine number 101 $cgI_2/g$, water content less than 0.1% w/w, freezing point 2° C., water solubility less than 0.004% w/w, and molecular weight 1654 Daltons. This polyol is available from BioBased Technologies, LLC as Agrol® 3.0.

Polyol-5: hydroxyl number 360 mg KOH/g, viscosity 3500 cP at 25° C., water content less than 0.1% w/w, molecular weight 730 Daltons, functionality 4.7, and special gravity 1.08 at 25° C. This polyol is available from Huntsman International LLC as Jeffol® SG360.

Mondur® MR-Light: NCO content of 31.0 minimum, acidity 0.01-0.03%, viscosity 150-250 cP at 25° C., equivalent weight 132, functionality 2.8, and special gravity 1.24. This isocyanate product is available from Bayer Materials Science, LLC.

T-12: Dibutyltin dilaurate, commercially available from Air Products as DABCO® T-12.

Titanium (IV) 2-ethylhexoxide: Commercially available from Johnson Matthey as Vertec® EHT.

Example 1

Synthesis of the Starting Natural Oil Polyols

The synthetic procedure for the starting polyols, that is, the hydroxylated vegetable oil esters, has been described in the U.S. patent application Ser. No. 10/924,332. With this procedure, natural oil polyols were synthesized with hydroxyl numbers of 69-195 mg KOH/g, viscosity 119-34800 cP at 25° C., and correspondingly the functionality ranged from 2.0 to 7.0.

Example 2

Five hundred grams of Polyol-3 were reacted with 56.82 grams of diethanolamine and 0.25 gram of titanium (IV) 2-ethylhexoxide in a three-necked flask. The reactants were heated to 90° C. with agitation for 2 hours and continued at 110° C. for 2 hr followed by 150° C. for 2.5 hours. The polyol that resulted possessed a hydroxyl number of 239 mg KOH/g and acid number of 0.21 mg KOH/g.

Example 3

Two hundred grams of Polyol-2 were reacted with 100 grams of diethanolamine and 0.1 gram of titanium (IV) 2-ethylhexoxide in a three-necked flask. The reactants were heated to 150° C. with agitation and continued to react at 140° C. for 24 hours. A polyol resulted with hydroxyl number of 450 mg KOH/g and viscosity of 5530 cP at 25° C.

Example 4

In a 15 gallon reactor containing 40.82 kg of the Polyol-2 were charged 8.16 kg of diethanolamine and 0.041 kg of titanium (IV) 2-ethylhexoxide at 140° C. under nitrogen. The reaction was continued at 140° C. for 12 hours and then the reaction mixture was cooled to 60° C. without any further purification steps. The resulting polyol had a hydroxyl number of 333 mg KOH/g and a viscosity of 2210 cP at 25° C.

Example 5

Two hundred grams of the Polyol-2 were reacted with 48 grams of diethanolamine and 0.2 gram of titanium (IV) 2-ethylhexoxide in a three-necked flask. The reactants were heated to 140° C. with agitation for 21 hours. A polyol was obtained with a hydroxyl number of 349 mg KOH/g and viscosity of 2590 cP at 25° C.

Example 6

Similar to the Example 5, the feed ratio was changed to 200 grams of Polyol-2, 75 grams of diethanolamine, and 0.2 gram of titanium (IV) 2-ethylhexoxide. A polyol was obtained with hydroxyl number of 426 mg KOH/g and viscosity of 4460 cP at 25° C.

Example 7

Two hundred grams of the Polyol-2 were reacted with 69 grams of diethanolamine, 50 grams of glycerol, and 0.2 gram of titanium (IV) 2-ethylhexoxide in a three-necked flask. The reactants were heated to 140° C. with agitation for 22 hours. A polyol was obtained with hydroxyl number of 501 mg KOH/g and viscosity of 4320 cP at 25° C.

Example 8

Seven hundred grams of the Polyol-4 were reacted with 134 grams of 2-(ethylamino) ethanol, and 0.1 gram of titanium (IV) 2-ethylhexoxide in a three-necked flask. The reactants were heated to 140° C. with agitation for 12 hours. A polyol was obtained with hydroxyl number of 256 mg KOH/g and viscosity of 260 cP at 25° C.

Example 9

Two hundred grams of the Polyol-3 were reacted with 60 grams of ethanolamine, and 0.2 gram of titanium (IV) 2-ethylhexoxide in a three-necked flask. The reactants were heated to 140° C. with agitation for 17 hours. A polyol was obtained with hydroxyl number of 296 mg KOH/g and melting point of 50-54° C.

Example 10

Freeze/Thaw Stability

The results of the freeze/thaw stability testing are presented in the Table 1.

TABLE 1

FREEZE/THAW STABILITY TEST ON INVENTIVE POLYOLS

| Inventive polyols | Initial appearance | Number Freeze/Thaw Cycles | | | | |
|---|---|---|---|---|---|---|
| | | 1 | 2 | 3 | 4 | 5 |
| Polyol example 3 | visually transparent Amber color liquid | x☐ | x | x | x | x |
| Polyol example 6 | same as above | x | x | x | x | x |
| Polyol example 5 | same as above | x | x | x | x | x |
| Polyol example 7 | same as above | x | x | x | —☐☐ | — |

☐= No visible phase separation, cloudy, and precipitation were observed.
☐☐= No test done under this condition Example 11

Reactivity Comparison

One hundred grams of polyols were mixed with Mondur® MR-Light at index 105 (1.05 NCO/OH molar ratio) at ambient temperature. The viscosity-curing time curve was then recorded following the BVT procedure. With 0.05 weight percent (based on polyol weight) T-12 (as catalyst), the gelation time of the Polyol-3, a starting hydroxylated vegetable oil, with Mondur® MR-Light is 16.5 minute. The inventive polyol from Example 4 has an 8 minute gelation time even without using any catalyst. By mixing 20 weight percent (based on the total weight of the polyols) of the polyol from Example 4 with 80 weight percent of the Polyol-3, the gelation time was recorded as 9 minutes with 0.015 weight percent of T-12 as the catalyst. The results show that the inventive polyol reacts with isocyanate much faster than the starting polyol does. By blending the inventive polyol with the starting polyol the reactivity of the polyol mixture is promoted significantly.

Example 12

Miscibility of Natural Oil Hydroxylates with a Selected Polyether Polyol

When 50 ml of Polyol-1 mixed with 50 ml of Polyol-5 in a cylinder was placed in a 70° C. oven for 12 hours, two phases with equal volumes were observed. This cylinder was removed from the oven and placed at ambient temperature for 3 days. At the end of three days, two phases with equal volumes were observed, which demonstrated that the Polyol-1 is not miscible with Polyol-5. The same experimental procedure was used for the test on the inventive polyol from the Example 4 and in one case with the Polyol-1 and in the other case with Polyol-5. One single phase was observed for the blend made either the inventive polyol with the Polyol-5 or the inventive polyol with the Polyol-1. The results demonstrate the inventive polyol from Example 4 is 100% v/v miscible with either the Polyol-1 or the Polyol-5.

Following the same test procedure, when 30 ml of Polyol-1 and 20 ml of the inventive polyol from Example 4 mixed with 50 ml of Polyol-5 in a cylinder and then placed in a 70° C. oven for 12 hours, no phase separation was observed; however, a color-gradient was observed from the bottom to the top of the liquid.

After placing the cylinder at ambient temperature for 3 days, two phases were observed with the 20 ml of upper layer and 80 ml of lower layer, which demonstrates 20% (v/v) of Polyol-1 was dissolved in Polyol-5 at ambient temperature. Further, there was mixed 25 ml of Polyol-1 and 50 ml of the inventive polyol with 25 ml of Polyol-5, one single phase was observed no matter whether at 70° C. for 12 hours or at ambient temperature for 3 days, which demonstrated Polyol-1 was 100% (v/v) dissolved in Polyol-5 with the help of the inventive polyol under these experimental conditions.

Example 13

Miscibility of the Inventive Polyols with Water

Both the starting natural oil hydroxylates and the inventive polyols are practically incompatible with water, for which the water solubility of the starting polyols and the inventive polyol from Example 4 are less than 0.004 weight percent at 25° C. Polyol-5 is completely miscible with water. When 10 ml of water and 30 ml of the inventive polyol was mixed with 20 ml of Polyol-5, one single phase was observed no matter whether at ambient temperature or at 70° C. However, in addition to the composition of water, the inventive polyol, and Polyol-5, when 20 ml of Polyol-1 and additional 10 ml of the Polyol-5 were added, two separated phases were observed after placing the liquid mixture at 70° C. for 12 hours. The results demonstrate that the improvement on the miscibility with water is relatively convenient to be made for the inventive polyols than for the starting polyols.

Example 14

Hardness

Fifty grams of polyol, including starting polyols and the inventive polyols, were mixed mechanically with Mondur® MR-Light (105 index), respectively, in different polyethylene plastic cups for at least 1 min and then placed in a 60° C. oven for 2 days for curing. The solid polyurethane materials were aged at ambient temperature at atmosphere for at least a week prior to hardness tests. Hardness values of the solid polyurethane material made with the Polyol-2 were measured as Shore A 80 and Shore D 22. Hardness values of the solid polyurethane material made with the inventive polyol from the Example 4 were measured as Shore A 96 and Shore D 78.

What is claimed is:

1. A process for preparing natural oil hydroxylates, said process comprising reacting an amino compound containing hydroxyl groups, said compound having a molecular weight of less than 200 Daltons and selected from the group consisting of primary and secondary amino compounds, with natural vegetable oil derived polyol having hydroxylated fatty acid triglyceride units for a time sufficient and at a temperature sufficient to provide natural oil hydroxylates having hydroxyl number values ranging from 240 to 530 mg KOH/g and a viscosity ranging from 260-5300 cP at 25° C.

2. A process as claimed in claim 1 wherein the natural oils that can be used for conversion into natural oil hydroxylates are those that contain triacylglycerols of saturated and unsaturated fatty acids.

3. A process as claimed in claim 2 wherein the natural oil is selected from the group comprising soybean oil, castor oil, palm oil, rapeseed oil, cotton oil, corn oil, sunflower oil, olive oil, canola oil, peanut oil, coconut oil, algae oil, and jatropha oil.

4. A process as claimed in claim 2 wherein the natural oil is selected from the group consisting essentially of soybean oil, canola oil, jatropha oil, algae oil, and palm oil.

5. A process as claimed in claim 1 wherein the amino compound containing hydroxyl groups having a molecular weight of less than 200 Daltons are those having secondary amine groups combined with at least one hydroxyl group in their molecular structures and having molecular weights ranging from 74 to 200 Daltons.

6. A process as claimed in claim 5 wherein the hydroxyalkylamine is selected from the group comprising: methylaminoethanol, diethanolamine, 2-(ethylamino)ethanol, N-benzylethanolamine, 2-anilimoethanol, 3-pyrrolidinol, prolinol, 3-piperidinol, 2-(isopropylamino)ethanol, 1-(2-hydroxyethylamino)propanol, 3-methylamino-1,2-propanediol, 2-piperidinemethanol, 2-(tert-butylamino)ethanol, 2-(butylamino)ethanol, 1-(2-aminoethylamino)-2-propanol, 2-(3-aminopropylamino)ethanol, 3-(-2-hydroxyethylamino)-1-propanol, 2-(2-ethylanilimo) ethanol, diisopropanolamine, 2-(2-(Methylamino)ethylamino)-ethanol, pyrrolidinol, prolinol, piperidinol, piperidinemethanol, and any combinations thereof.

7. A process as claimed in claim 1 wherein there is also present a catalyst.

8. A process as claimed in claim 7 wherein the catalyst is present at 0.05-0.20 weight percent based on the weight of the starting hydroxylated vegetable oil esters.

9. A process as claimed in claim 1 wherein the temperature is in the range of 90-200° C.

10. A process as claimed in claim 1 wherein the temperature is in the range of 120° C. to 150° C.

11. A process as claimed in claim 1 wherein the vacuum is in the range of 0.5 to 200 torr for 0.5 to 3 hours.

12. A process for preparing natural oil hydroxylates, said process comprising contacting a raw vegetable oil with hydrogen peroxide and an organic acid in the presence of water for a sufficient period of time, a sufficient temperature, and a sufficient pressure to form hydroxyl groups from unsaturated moieties in the vegetable oil, and thereafter separating any volatiles from the hydroxylated functional vegetable oil, wherein the organic acid has from 1 to 3 carbon atoms, thereafter, contacting the hydroxylated functional vegetable oil with an amino compound containing hydroxyl groups having a molecular weight of less than 200 Daltons, said amino compound selected from the group consisting of primary, and secondary amines.

13. A process as claimed in claim 12 wherein there is present a catalyst for the amino compound having hydroxyl groups and polyol reaction.

14. A process as claimed in claim 13 wherein the catalyst is an organometallic compound.

15. A process as claimed in claim 1 wherein the natural vegetable oil hydroxylate contains 0-94 weight percent of hydroxylated fatty acid hydroxyalkylamide, 0-34 weight percent of hydroxylated mono-glyceride esters, 0-64 weight percent of hydroxylated diglyceride esters, and 0-16 weight percent of glycerol.

16. A process as claimed in claim 1 wherein the natural vegetable oil hydroxylate contains 36-94 weight percent of hydroxylated fatty acid hydroxyalkylamide, 0-34 weight percent of hydroxylated mono-glyceride esters, 0-64 weight percent of hydroxylated diglyceride esters, and 0-6 weight percent of glycerol.

17. A process as claimed in claim 1 wherein the natural vegetable oil hydroxylate contains 51-84 weight percent of hydroxylated fatty acid hydroxyalkylamide, 13-31 weight percent of hydroxylated mono-glyceride esters, 0-21 weight percent of hydroxylated diglyceride esters, and 0-3 weight percent of glycerol.

18. A process as claimed in claim 1 wherein the natural oil hydroxylates contains compounds selected from the group consisting essentially of a) fatty acid monoalkanolamide, b) fatty acid dialkanolamide; c) natural oil diglyceride, d) natural oil monoglyceride, e) glycerin and f) mixtures of natural monoglycerides, wherein the fatty acid groups may also contain acetate or methoxide groups.

19. A composition of matter comprising a natural oil hydroxylate having at least one hydroxylated fatty amide unit.

20. A process for making the inventive polyols by reacting natural oil hydroxylates and hydroxyalkylamines as starting materials at elevated temperature in the presence of catalysts.

21. A process according to claim 1 further comprising the step of contacting the natural oil hydroxylate with an isocyanate.

22. A composition of matter according to claim 19 further comprising a natural oil hydroxylate having at least one hydroxylated fatty amide unit and at least one hydroxylated fatty acid unit selected from the group consisting of monoglyceride units and diglyceride units.

23. A composition of matter according to claim 19 having a hydroxyl number value ranging from 240 to 530 mg KOH/g and a viscosity ranging from 260-5300 cP at 25° C.

* * * * *

UNITED STATES PATENT AND TRADEMARK OFFICE
CERTIFICATE OF CORRECTION

PATENT NO. : 8,097,739 B2
APPLICATION NO. : 12/082808
DATED : January 17, 2012
INVENTOR(S) : Ning Luo et al.

It is certified that error appears in the above-identified patent and that said Letters Patent is hereby corrected as shown below:

On the title page and col. 1, line 1, in the Title delete "Process for the manufacture of natural oil hydroxylates" and insert -- A process for the manufacture of natural oil hydroxylates --, therefor.

Signed and Sealed this
Third Day of April, 2012

David J. Kappos
*Director of the United States Patent and Trademark Office*